United States Patent [19]

Mautner et al.

[11] Patent Number: 5,502,230
[45] Date of Patent: Mar. 26, 1996

[54] PROCESS FOR PREPARING HYDROGEN-CONTAINING METHYLCHLOROSILANES

[75] Inventors: Konrad Mautner, Kastl; Ulrich Goetze, Burghausen; Anton Schinabeck, Burghausen; Wilfried Kalchauer, Burghausen, all of Germany

[73] Assignee: Wacker-Chemie GmbH, Munich, Germany

[21] Appl. No.: 514,529

[22] Filed: Aug. 14, 1995

[30] Foreign Application Priority Data

Sep. 8, 1994 [DE] Germany .................... 44 31 995.9

[51] Int. Cl.[6] .................................................. C07F 7/08
[52] U.S. Cl. .................................................. 556/468
[58] Field of Search .................................................. 556/468

[56] References Cited

U.S. PATENT DOCUMENTS

| | | | |
|---|---|---|---|
| 4,059,607 | 11/1977 | Reedy et al. | 556/468 |
| 4,363,925 | 12/1982 | Acker et al. | 556/468 X |
| 5,292,909 | 3/1994 | Chadwick et al. | 556/468 |
| 5,292,912 | 3/1994 | Chadwick et al. | 556/468 |
| 5,326,896 | 7/1994 | Chadwick et al. | 556/468 X |

FOREIGN PATENT DOCUMENTS

| | | |
|---|---|---|
| 274227 | 12/1989 | German Dem. Rep. . |
| 54-9228 | 1/1979 | Japan . |

OTHER PUBLICATIONS

Journal of Organometallic Chemistry, 225 (1982) 117–130, R. Calas et al. "Some practical uses of the disilane residue from the direct . . . ".

German translation of JP–A 54–9228, Jan. 1979.

Primary Examiner—Paul F. Shaver
Attorney, Agent, or Firm—Martin Connaughton

[57] ABSTRACT

In the process of the present invention, disilanes are reacted with hydrogen chloride in the presence of a catalyst comprising
(A) palladium(O) or platinum(O), and
(B) an organic compound selected from among tertiary amines, carboxamides, alkylureas, tertiary phosphines, phosphoramides, quaternary ammonium halides, quaternary phosphonium halides or mixtures thereof to give hydrogen-containing methylchlorosilanes.

9 Claims, No Drawings

PROCESS FOR PREPARING HYDROGEN-CONTAINING METHYLCHLOROSILANES

FIELD OF INVENTION

The present invention relates to a process for preparing hydrogen-containing methylchlorosilanes by cleavage of disilanes with hydrogen chloride in the presence of a catalyst comprising (A) palladium(O) or platinum(O) and (El) an organic compound selected from among tertiary amines, carboxamides, alkylureas, tertiary phosphines and phosphoramides, quaternary ammonium halides, quaternary phosphonium halides or mixtures thereof.

In the direct synthesis of methylchlorosilanes by the Müller-Rochow method from silicon and chloromethane at from 250° to 300° C. using copper catalysts, disilanes are obtained as by-products. The main disilanes formed are 1,1,2,2-tetrachlorodimethyldisilane and 1,1,2-trichlorotrimethyldisilane. Together with 1,1-dichlorotetramethyldisilane, they can be cleaved to give monosilanes by catalyzed reaction with hydrogen chloride. In R. Calas et al., J. Organometall. Chem., 225, 117, 1982, the catalysts used are tertiary amines or amides and in DD-A 274 227 alkylureas or phosphoramides are used as catalyst. The main products formed are methyltrichlorosilane, dimethyldichlorosilane and methyldichlorosilane. The theoretical yield of methyldichlorosilane is not achieved, since, in a side reaction, the hydrogen-containing silane reacts with hydrogen chloride with elimination of hydrogen to give a chlorosilane.

1,2-dichlorotetramethyldisilane, chloropentamethyldisilane and hexamethyldisilane cannot be cleaved using the above mentioned catalysts and hydrogen chloride. In JP-A 54-9228, tetrakis(triphenylphosphine)palladium(O) is used as catalyst for the cleavage of methylchlorodisilanes, including 1,2-dichlorotetramethyldisilane. Hydrogen containing monosilanes are obtained, however, the yield over time is very low.

SUMMARY OF INVENTION

It is an object of the present invention to provide a catalyst for cleaving all the disilanes obtained in the methylchlorosilane synthesis, which cleaves the disilanes and improves the yield of hydrogen-containing methylchlorosilanes.

The invention provides a process for preparing hydrogen-containing methylchlorosilanes of the formula

  (I)

which comprises reacting disilanes of the formula

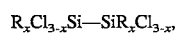  (II)

where, in formulae (I) and (II),
R is a hydrogen atom, a methyl, phenyl or ethyl radical and x is 0, 1, 2 or 3,
with hydrogen chloride in the presence of a catalyst comprising
(A) palladium(O) or platinum(O) and
(B) an organic compound selected from among tertiary amines, carboxamides, alkylureas, tertiary phosphines, phosphoramides, quaternary ammonium halides, quaternary phosphonium halides or mixtures thereof.

The process cleaves all disilanes. At the same time, catalyst constituent (A) has a moderating effect on the catalyst constituent {B}, so that the yield of hydrogen-containing methylchlorosilanes is high.

The disilanes used can additionally contain methylchlorosilanes, hydrocarbons, chlorinated hydrocarbons, carbosilanes and siloxanes. The disilane content is preferably at least 50% by weight.

The hydrogen chloride is preferably added in gaseous form. Preferably, from 1 to 4 mole of hydrogen chloride, in particular from 1 to 1.5 mole of hydrogen chloride, are used per mole of Si—Si bonds. Since hydrogen chloride is present as gas at suitable temperatures and pressures, it is very easy to separate off from the methylchlorosilanes after the reaction. Commercial hydrogen chloride can be used.

The catalyst constituent (A) used can be palladium or platinum in the oxidation state (O) either in metallic form or as complexes.

Preferred complexes are compounds soluble in the disilane mixture and in the methylchlorosilanes prepared. Examples of preferred complexes are tetrakis-(triphenylphosphine)-palladium(O), tetrakis-(triphenylphosphine)-platinum(O), bis-[bis-(1,2-diphenylphosphine)ethane]-palladium(O) and tetrakis-(methyldiphenylphosphine)-palladium(O). More preference is given to tetrakis-(triphenylphosphine)-palladium(O) and tetrakis-(triphenyl-phosphine)-platinum(O).

If palladium or platinum are used in metallic form, they can be used in any desired form, for example as gauze or foil or in finely divided form. The metals are preferably applied to supports, so they can be used for example, in a fixed-bed reactor through which the reaction mixture flows, such as a distillation column or a flow-through reactor. The supports are then preferably in the form of pieces, to keep the pressure drop when disilanes of formula (II) are passed through as small as possible.

More preference is given to metals on pulverulent supports, to be used for example, in circulation evaporators of distillation columns or reactors.

Suitable support materials are all usual materials, such as carbons and ceramic supports. Examples of supports are activated carbon and inorganic oxides such as silicon dioxide, aluminum(III)oxide, silicates, titanium dioxide, zirconium dioxide; carbides such as silicon carbide; with activated carbon and silicon dioxide being preferred examples. As catalyst A, more preference is given to palladium on activated carbon.

Such catalysts (A) in which the finely divided metals are located on supports, can be prepared by reduction of metal compounds in the presence of the support.

The concentration of the metals on the supports is preferably from 0.5% to 5% by weight, based on the total weight of the support and the metal; but it is also possible to use higher or lower concentrations.

The proportion of palladium or platinum in the oxidation state (O) in the catalyst constituent A is preferably at least 3 mole % and preferably at least 25 mole % based on all catalyst constituents.

The tertiary amines B preferably contain alkyl radicals or aryl radicals having from 1 to 10 carbon atoms, which radicals can be substituted by halogen atoms. Examples of preferred tertiary amines are tributylamine, trioctylamine, triisononylamine and triphenylamine.

It is also possible to use bridged diamines or triamines, such as tetramethylethylenediamine and diaza[2.2.2]bicyclooctane.

The tertiary amines also include heterocycles having 3 to 7-membered rings, including fused heterocycles, having at least one basic nitrogen atom and 2 to 10 carbon atoms. The rings can have $C_1$-$C_{10}$-alkyl and/or halogen substituents. Examples are pyrazole, pyridine, quinoline, 2,5-dimethylpyridine and 2-chloroquinoline.

The carboxamides B are preferably amides of alkylcarboxylic acids or arylcarboxylic acids having from 1 to 10 carbon atoms, which amides are substituted by 2 alkyl radicals or aryl radicals each having from 1 to 10 carbon atoms. The aryl or alkyl radicals of the carboxylic acids and on the nitrogen atom can be substituted by halogen atoms. Also preferred are cyclic carboxamides, an alkyl radical of which on the nitrogen atom is joined to the alkyl radical on the carboxylic acid to give a heterocyclic ring comprising 5 or 6 ring atoms. Examples of preferred carboxamides and N,N-dimethylformamide, 1-methyl-2-pyrrolidone, N,N-diethylformamide and N,N-dimethylbenzamide.

The alkylureas B preferably contain alkyl radicals having from 1 to 10 carbon atoms, which radicals can be substituted by halogen atoms. Also preferred are cyclic alkylureas in which two alkyl radicals are joined to one another to give a heterocyclic ring comprising 5 or 6 ring atoms. Examples of preferred alkylureas are tetramethylurea, 1,3-dimethyl-3,4,5,6-tetrahydro- 2( 1H)-pyrimidone (DMPU).

The tertiary phosphines B preferably contain 2 or 3 aryl radicals each having from 6 to 20 carbon atoms. The aryl radicals may be unsubstituted or substituted by alkyl radicals having from 1 to 10 carbon atoms and halogen atoms.

Examples of preferred tertiary phosphines and triphenylphosphines which may be unsubstituted or substituted by a halogen atom or at most three alkyl radicals having from 1 to 10 carbon atoms are triphenylphosphine and bis(diphenylphosphino)ethane.

The phosphoramides B are preferably substituted by 6 alkyl radicals each having from 1 to 10 carbon atoms. The alkyl radicals can be substituted by halogen atoms. Examples of preferred phosphoramides are hexamethylphosphoramide (HMPT), and hexaethylphosphoramide.

The quaternary ammonium halides preferably contain alkyl, alkaryl or aryl groups having 1 to 20 carbon atoms and may be unsubstituted or substituted by halogen atoms. Examples are tetramethylammonium chloride, tetrabutylammonium chloride, methyltrioctylammonium chloride, benzyltrimethylammonium chloride and distearyldimethylammonium chloride.

The quaternary ammonium halides also include N-alkylated heterocycles having 3 to 7-membered rings, including fused heterocycles, having 2 to 10 carbon atoms. The rings can have $C_1$-$C_{10}$-alkyl and/or halogen substituents. A preferred example is N-methylpyridinium chloride.

The quaternary phosphonium halides preferably contain alkyl, alkaryl or aryl groups having 1 to 20 carbon atoms and may be unsubstituted or substituted by halogen atoms. Examples are methyltriphenylphosphonium chloride, tetrabutylphosphonium chloride and tetraphenylphosphonium chloride.

More preference is given to using the combination of palladium metal on a support with tertiary phosphines.

As halogen atoms which function as substituents or as counterions of the catalyst constituent B, preferance is given to fluorine, chlorine and bromine. More preference is given to chlorine.

Based on the amount of disilanes present in the reactor, use is preferably made of from 0.5% to 20% by weight of the total weight of catalyst constituents A and B, in particular from 1% to 5% by weight.

The process can be carried out batchwise, semi-continuously or fully continuously, with preference being given to using the fully continuous procedure. In particular, the process is carried out continuously at the boiling point in a reactor having a distillation unit fitted on top. The disilanes of formula (II) and hydrogen chloride are metered in at the rate at which resulting hydrogen-containing methylchlorosilanes of formula (I) together with hydrogen-free methylchlorosilanes are distilled off.

The reaction temperature is preferably at least 100° C. The reaction preferably takes place at from 0.08 to 0.8 MPa.

Examples of hydrogen-containing methylchlorosilanes of formula (I) are methyldichlorosilane, dimethylchlorosilane and trimethylsilane. The methylchlorosilanes such as methyltrichlorosilane, dimethyldichlorosilane, trimethylchlorosilane and tetrachlorosilane likewise formed in the process are likewise valuable products.

In the following examples, unless otherwise indicated:
(a) all amounts are by weight;
(b) all pressures are 0.10 MPa (abs.);
(c) all temperatures are 20° C.

EXAMPLES

Examples 1 to 3

A 4 liter flask provided with a distillation unit fitted on top and a gas inlet tube for hydrogen chloride was charged with the catalyst and 2 liters of a disilane mixture. Hydrogen chloride was added and the mixture was heated to boiling at atmospheric pressure (reactor temperature 140° C.). The disilane mixture was added via a metering device in such a way that the level in the reactor did not change. The products distilled off were condensed and analyzed. The disilane mixture consisted mainly of 1,1,2,2-tetrachlorodimethyldisilane and 1,1,2-trichlorotrimethyldisilane and in addition 1,2-dichlorotetramethyldisilane, chloropentamethyldisilane, hexamethyldisilane and small amounts of monosilanes and hydrocarbons. The results are given in Table I.

Example 1 (not according to the invention)
   Catalyst: tributylamine
Example 2 (not according to the invention)
   Catalyst: tetrakis-(triphenylphosphine)-palladium(O)
Example 3 [according to the invention]
   Catalyst: tributylamine (95 mole %) and tetrakis-(triphenylphosphine)-palladium(O)
   (5 mole %)

Example 3 shows that the combination of catalyst constituents A and B can significantly increase the proportion of hydrogen-containing silanes compared with the individual catalyst constituents. Use of tetrakis-(triphenylphosphine)-palladium(O) results in the formation of dimethylchlorosilane which originates from the cleavage of 1,2-dichlorotetramethyldisilane and chloropentamethylsilane. However, the yield over time for the pure Pd(O) complex is significantly lower.

TABLE I

| Example | | 1 | 2 | 3 |
|---|---|---|---|---|
| Catalyst amount | [g] | 15.5 | 5 | 20.5 |
| Amount of Pd(0) complex included in above | | — | 5 | 5 |
| Metering rate of disilane mixture | [g/h] | 200 | 60 | 200 |
| Reactor temperature | [°C.] | 140 | 140 | 140 |
| Temperature at top | [°C.] | 60 | <90 | 55 |
| Amount of distillate | [g/h] | 210 | 60 | 205 |
| Composition: | | | | |
| Dimethylchlorosilane | [% by weight] | 0 | 0.5 | 0.2 |
| Methyldichlorosilane | [% by weight] | 28 | 8 | 46.9 |
| Trimethylchlorosilane | [% by | 0.7 | 2.5 | 0.9 |

TABLE I-continued

| Example | | 1 | 2 | 3 |
|---|---|---|---|---|
| Methyltrichlorosilane + dimethyldichlorosilane | [% by weight] | 70.7 | 72.4 | 51.1 |

Example 4 and 5

The examples were carried out using a method similar to Examples 1 to 3. The results are given in Table II.
Example 4 [not according to the invention]
  Catalyst: triphenylphosphine
Example 5 (according to the invention)
  Catalyst: triphenylphosphine (97 mole %) and tetrakis-(triphenylphosphine)-palladium(O) (3 mole %)

TABLE II

| Example | | 4 | 5 |
|---|---|---|---|
| Catalyst amount | [g] | 40 | 45 |
| Amount of Pd(0) complex included in above | | — | 5 |
| Metering rate of disilane mixture | [g/h] | 180 | 150 |
| Reactor temperature | [°C.] | 140 | 140 |
| Temperature at top | [°C.] | 55 | 55 |
| Amount of distillate | [g/h] | 185 | 150 |
| Composition: | | | |
| Dimethylchlorosilane | [% by weight] | 0 | 0.8 |
| Methyldichlorosilane | [% by weight] | 5.1 | 28.2 |
| Trimethylchlorosilane | [% by weight] | 2.4 | 1.5 |
| Methyltrichlorosilane + dimethyldichlorosilane | [% by weight] | 90.4 | 61.8 |

Example 6 and 7

The examples were carried out using a method similar to Examples 1 to 3. The results are given in Table III.
Example 6 {not according to the invention)
  Catalyst: 3% palladium on activated carbon (type K 0224 from W. C. Heraeus GmbH, Hanau)
Example 7 [according to the invention)
  Catalyst: 3% palladium on activated carbon {as in Example 6) and triphenylphosphine

TABLE III

| Example | | 6 | 7 |
|---|---|---|---|
| Catalyst amount | [g] | 25 | 65 |
| Amount of Pd(0) activated carbon included in above | | 25 | 25 |
| Metering rate of disilane mixture | [g/h] | 120 | 180 |
| Reactor temperature | [°C.] | 140 | 140 |
| Temperature at top | [°C.] | 60 | 60 |
| Amount of distillate | [g/h] | 125 | 190 |
| Composition: | | | |
| Dimethylchlorosilane | [% by weight] | 0 | 1.1 |
| Methyldichlorosilane | [% by weight] | 0.6 | 26.7 |
| Trimethylchlorosilane | [% by weight] | 0.7 | 1.9 |
| Methyltrichlorosilane + dimethyldichlorosilane | [% by weight] | 91.3 | 60.6 |

What is claimed is:

1. A process for preparing hydrogen-containing methylchlorosilanes of the formula $$R_xCl_{3-x}SiH, \qquad (I)$$

which comprises reacting disilanes of the formula $$R_xCl_{3-x}Si-SiR_xCl_{3-x}, \qquad (II)$$

where, in the formulae I and II,
R is a hydrogen atom, a methyl, phenyl or ethyl radical and
x is 0, 1, 2 or 3,
with hydrogen chloride in the presence of a catalyst comprising
(A) palladium(O) or platinum(O) and
(B) an organic compound selected from among tertiary amines, carboxamides, alkylureas, tertiary phosphines, phosphor amides, quaternary ammonium halides, quaternary phosphonium halides or mixtures thereof.

2. The process as claimed in claim 1, wherein catalyst constituent A palladium(O) or platinum(O) is present in metallic form or as a complex.

3. The process as claimed in claim 1, wherein the catalyst constituent B is a tertiary amine containing alkyl radicals having from 1 to 10 carbon atoms, and is optionally substituted by halogen atoms.

4. The process as claimed in claim 1, wherein the catalyst constituent B is a carboxamide which is the amide of an alkylcarboxylic acid having from 1 to 10 carbon atoms, which is substituted by 2 alkyl radicals each having from 1 to 10 carbon atoms, where the alkyl radicals of the carboxylic acid and on the nitrogen atom are optionally substituted by halogen atoms and where in the carboxamides an alkyl radical on the nitrogen atom are optionally joined to the alkyl radical on the carboxylic acid to give a heterocyclic ring having 5 or 6 ring atoms.

5. The process as claimed in claim 1, wherein the catalyst constituent B used is an alkylurea containing alkyl radicals having from 1 to 10 carbon atoms, which radicals are optionally substituted by halogen atoms and where in the alkylureas two alkyl radicals are optionally joined to one another to give a heterocyclic ring comprising 5 or 6 ring atoms.

6. The process as claimed in claim 1, wherein the catalyst constituent B is a tertiary phosphine containing 3 aryl radicals each having from 6 to 20 carbon atoms, which aryl radicals are optionally substituted by alkyl radicals having from 1 to 10 carbon atoms and halogen atoms.

7. The process as claimed in claim 1, wherein the catalyst constituent B is a phosphoramide substituted by 6 alkyl radicals each having from 1 to 10 carbon atoms, which radicals are optionally substituted by halogen atoms.

8. The process as claimed in claim 1, wherein the catalyst constituent B is a quaternary ammonium halide containing 3 aryl or alkyl radicals each having from 1 to 20 carbon atoms, which radicals are optionally substituted by halogen atoms.

9. The process as claimed in claim 1, wherein the catalyst constituent B is a quaternary phosphonium halide containing 3 aryl or alkyl radicals each having from 1 to 20 carbon atoms, which radicals are optionally substituted by halogen atoms.

* * * * *